United States Patent [19]

Mak et al.

[11] Patent Number: 4,720,491
[45] Date of Patent: Jan. 19, 1988

[54] FLUORALKYLATEDCARBAPENEM DERIVATIVES

[75] Inventors: Ching P. Mak; Hans Fliri, both of Vienna, Austria

[73] Assignee: Sandoz Ltd., Tokyo, Japan

[21] Appl. No.: 793,017

[22] Filed: Oct. 30, 1985

Related U.S. Application Data

[63] Continuation of Ser. No. 657,220, Oct. 3, 1984, abandoned.

[51] Int. Cl.$^4$ .................... C07D 487/04; A61K 31/40
[52] U.S. Cl. .................................. 514/210; 540/350; 540/200
[58] Field of Search ................ 260/245.2 R; 540/350; 514/210

[56] References Cited

U.S. PATENT DOCUMENTS 4,312,871 1/1982 Christensen et al. .......... 260/245.25

Primary Examiner—Nicholas S. Rizzo
Attorney, Agent, or Firm—Robbins & Laramie

[57] ABSTRACT

Compounds of formula I

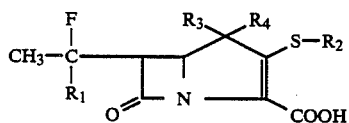

wherein, $R_1$ represents hydrogen or methyl, $R_2$ represents hydrogen or lower alkyl, lower alkenyl, lower alkynyl or cycloalkyl each of which may be unsubstituted or mono- or poly-substituted by amino, mono- or di(lower)-alkylamino, lower acylamino, carboxy, lower alkoxycarbonyl or carbamoyl; a group of formula IIc $(CH_2)_p-R_5$   IIc wherein $R_5$ represents phenyl or a 5- or 6-membered saturated or unsaturated heterocycle containing one or more heteroatoms selected from O, S and/or N and which may be unsubstituted or mono- or poly-substituted by fluoro, chloro, bromo, amino, mono- or di-(lower)-alkylamino, hydroxy, lower alkoxy, mercapto, alkylthio, phenylthio, sulfamoyl, guanidino, nitro, cyano, lower acylamino, carboxy, alkoxycarbonyl or carbamoyl and p is 0, 1, 2 or 3; or a group of formula

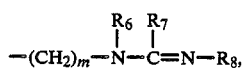

II

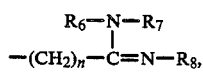

IIa

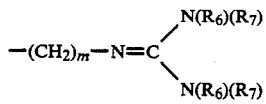

IIb wherein $R_6$, $R_7$ and $R_8$ may be the same or different and each represents hydrogen or lower alkyl or $R_6$ and $R_8$ and/or $R_7$ and one of the $CH_2$ groups may be joined to form a ring as may $R_7$ and $R_8$ in formula II and $R_6$ and $R_7$ in IIa and IIb, which rings may be unsubstituted or mono- or poly-substituted by alkyl, hydroxy, carboxy or di-(lower)-alkyl-amino, m is 2 or 3, and
n is 1, 2 or 3

$R_3$ represents hydrogen or lower alkyl and
$R_4$ represents lower alkyl, which are indicated for use as pharmaceuticals particularly as antibacterially active antibiotics.

6 Claims, No Drawings

FLUORALKYLATEDCARBAPENEM DERIVATIVES

This is a continuation of application Ser. No. 657,220, filed Oct. 3, 1984, now abandoned.

The present invention concerns 6-(1'-fluorethyl)- and 6-(1'-fluoro-1'-methylethyl)-carbapenems, processes for their production and their use as chemotherapeutics.

EP No. 10317 discloses a very wide range of carbapenem derivatives having antibiotic activity but makes no mention of the fluoralkylated compounds of the present invention and their advantageous antibiotic properties.

More particularly the invention concerns compounds of formula I

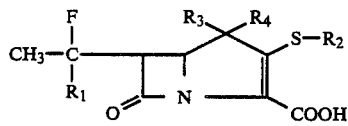

wherein,
$R_1$ represents hydrogen or methyl,
$R_2$ represents hydrogen or lower alkyl, lower alkenyl, lower alkynyl or cycloalkyl each of which may be unsubstituted or mono- or poly-substituted by amino, mono- or di-(lower)-alkylamino, lower acylamino, carboxy, lower alkoxycarbonyl or carbamoyl; a group of formula IIc $(CH_2)_p$—R    IIc wherein $R_5$ represents phenyl or a 5- or 6-membered saturated or unsaturated heterocycle containing one or more heteroatoms selected from O, S and/or N and which may be unsubstituted or mono- or poly-substituted by fluoro, chloro, bromo, amino, mono- or di-(lower)-alkylamino, hydroxy, lower alkoxy, mercapto, alkylthio, phenylthio, sulfamoyl, guanidino, nitro, cyano, lower acylamino, carboxy, alkoxycarbonyl or carbamoyl and p is 0, 1, 2 or 3; or a group of formula

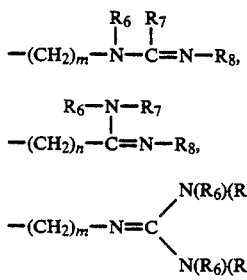

wherein
$R_6$, $R_7$ and $R_8$ may be the same or different and each represents hydrogen or lower alkyl or $R_6$ and $R_8$ and/or $R_7$ and one of the $CH_2$ groups may be joined to form a ring as may $R_7$ and $R_8$ in formula II and $R_6$ and $R_7$ in IIa and IIb, which rings may be unsubstituted or mono- or poly-substituted by alkyl, hydroxy, carboxy or di-(lower)-alkylamino,
m is 2 or 3, and
n is 1, 2 or 3

$R_3$ represents hydrogen or lower alkyl and
$R_4$ represents lower alkyl, or protected forms and/or physiologically hydrolysable and acceptable ester forms thereof; in free acid or salt form or in the form of zwitter-ions.

The compounds of the invention may be prepared
(A) by introducing a group —S—$R_2$ into a compound of formula III

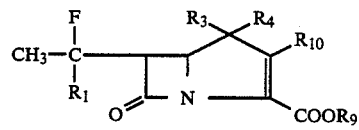

wherein
$R_1$ to $R_4$ are as defined above,
$R_{10}$ represents a leaving group
$R_9$ represents a protecting group or a physiologically hydrolysable and acceptable ester group or
(B) by exchanging the OH group in a compound of formula IV

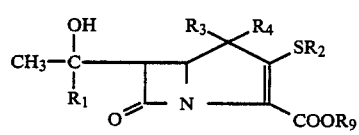

or a precursor thereof for fluoro, whereby in formula IV, $R_1$ to $R_4$ and $R_9$ are as defined above, and if required deprotecting a compound thus obtained or if required converting a compound thus obtained into or into another physiologically hydrolysable—and acceptable—ester form and/or protected form thereof and recovering the compound thus obtained in free acid or salt form or in the form of a zwitterion.

Process (A) may be carried out in conventional manner for example in an inert solvent such as an aromatic hydrocarbon e.g. benzene; or acetonitrile and preferably at reduced temperatures e.g. ca 0° C.

Process (B) may be carried out in conventional manner e.g. employing a dialkylaminosulfurtrifluoride such as diethylaminosulfurtrifluoride.

The removal of protecting groups is carried out in conventional manner as is the isolation and purification of the products obtained.

The preparation and interconversion of ester, protected and salt forms is also carried out in conventional manner.

Processes for preparing carbapenems in their various forms are also described in the literature for example in European patent application Publications Nos. 1628, 10316, 10317, 17992, 37080, 37081, 38869, 50334, 33209, 44142, 60612, 61231, 44170, 59478, 58317 and can where appropriate be employed analogously for preparing compounds according to the invention.

The starting materials of formula II are new and can be prepared by introducing the group $R_{10}$ into a compound of formula V

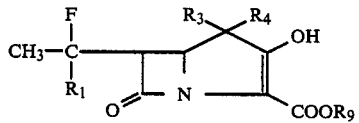

wherein $R_1$, $R_3$, $R_4$, $R_9$ and $R_{10}$ are as defined above.

Examples of leaving groups $R_{10}$ are those formed by reaction of the hydroxy group with a phosphoricacid-ester chloride e.g. with phosphoric acid diphenylester chloride or with a sulphonic acid e.g. with p-toluene sulphonic acid.

The compounds of formula IV can be prepared analogously to process (A) above from compounds of formula Va

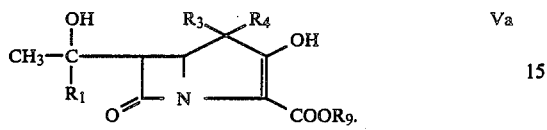

The process is conventional and comprises introduction of the group $R_{10}$ and replacement of this by the group $-S-R_2$.

The compounds of formula V are also new and can be prepared for example according to the following reaction schemes or analogously to methods described in the above mentioned reaction schemes.

REACTION SCHEME 1

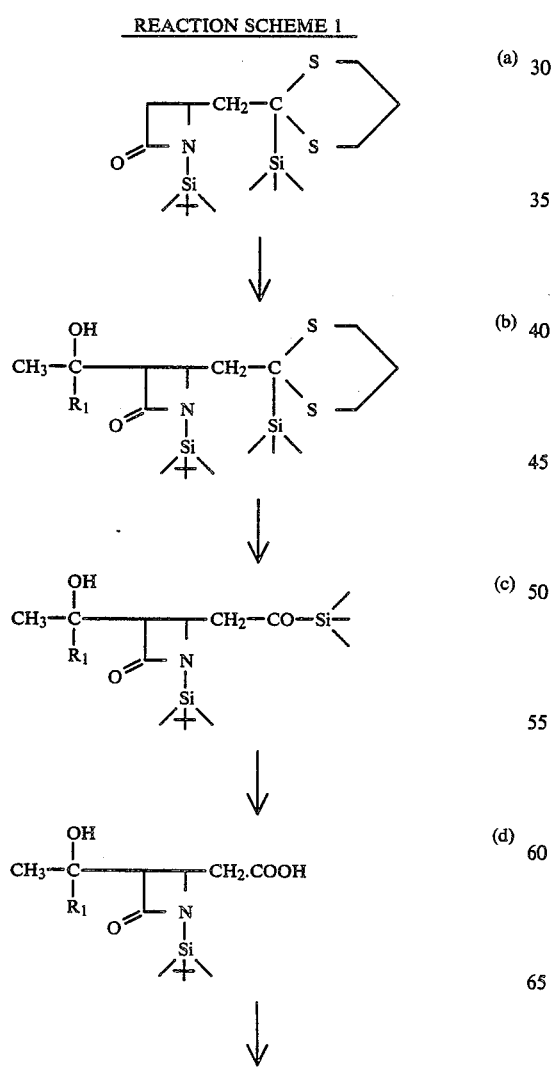

-continued
REACTION SCHEME 1

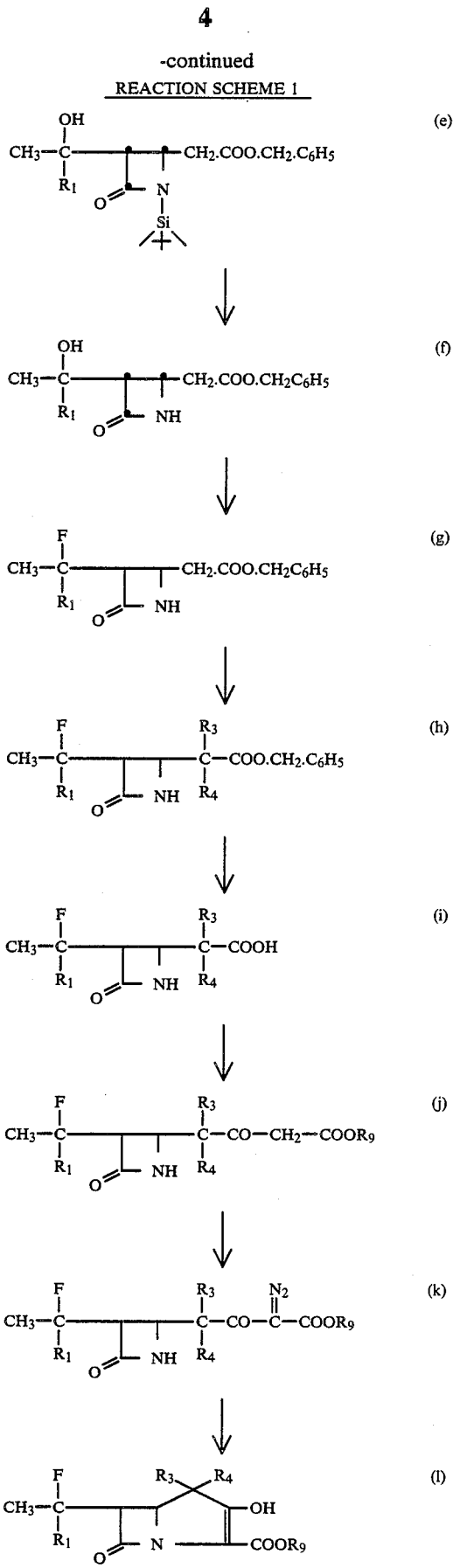

REACTION SCHEME 2

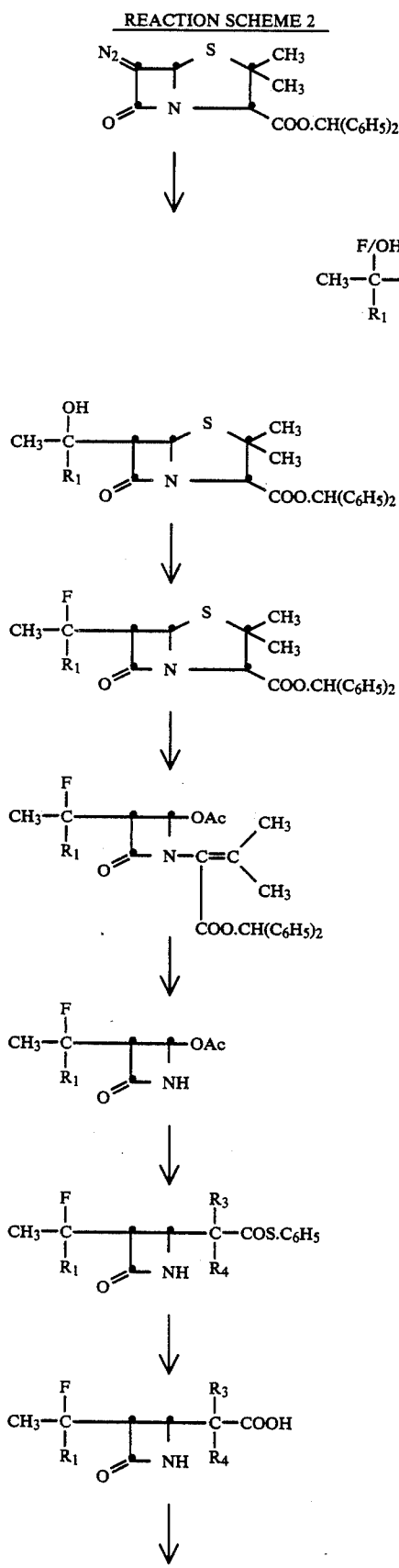

continue as in reaction scheme (Ii).

The reactions shown in these schemes can be carried out using procedures conventional for the type of reaction involved. Cyclisation can for example be carried out in an inert solvent such as an aromatic hydrocarbon e.g. benzene in the presence of a transitional metal catalyst. Examples of a transitional metal catalyst are rhodium(II)-acetate or copper acetylacetonate.

The compounds of formula V and Va can exist in the following tautomeric forms

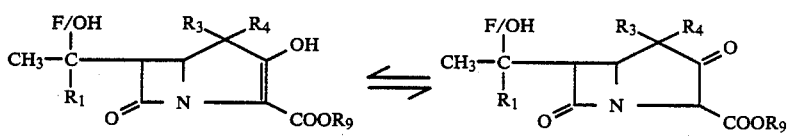

The remaining intermediates are either known or can be prepared analogously to known methods and/or as described hereinafter in the examples.

Carbapenems such as those of the present application contain 2 centres of chirality in the beta-lactam ring (5 and 6)

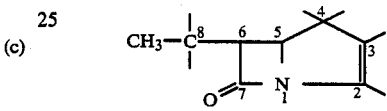

They can be present in the various configurations as 6R,5R-, 6S,5R-, 6R,5S- or 6S,5S-isomers or as mixtures thereof. When $R_3$ and $R_4$ are different a further assymetric carbon atom exists at position 4 and this has preferably the R-configuration. When the starting materials employed are in a particular configuration the end products obtained will have the same configuration and mixed starting materials will produce mixed end products. The configuration of these compounds thus does not alter during reactions such as (A) or (B) above. Mixtures of isomers can be separated by conventional methods such as fractional crystallisation.

It is known that the biological activity can be attributed to compounds, wherein the 5-position is in R-configuration.

A further centre of chirality is present when $R_1$ is hydrogen and this also remains unaffected during reactions such as (A) above. In reactions such as (B), however, where fluorine is introduced, inversion occurs. Thus fluorination of an 8-R-hydroxy starting material will yield an 8-S-fluoro end product and vice-versa.

The compounds of formula I in free form or physiologically-hydrolysable and acceptable ester form exhibit chemotherapeutic, in particular anti-microbial activity as indicated by their inhibiting effect against various bacteria, e.g. *Pseudomonas aeroginosa, Enterobacter cloacae, Enterobacter agglomerans, Staphylococcus epidermidis, Streptococcus aronson, Streptococcus pneumoniae, Aerococcus viridans, Staphylococcus aureus, Streptococcus pyogenes, Streptococcus faecalis, Escherichia coli, Proteus vulgaris, Proteus mirabilis, Proteus morganii, Klebsiella pneumoniae, Serratia marcescens* and *Salmonella typhimurium* in vitro in series dilution tests at concentrations of, for example, 0.001 to 50 ug/ml, and in vivo in the mouse at dosages of, for example, about 0.1 to 100 mg/kg of animal body weight.

The compounds also possess an inhibiting effect against β-lactamases at concentration between 0.1 and 10 ug/ml. The enzymatic activity of β-lactamase-preparations of gram-positive and gram-negative bacteria may be tested using the chromogenic substrate Nitrocefin (Lit: C. H. O'Callaghan et.al., Novel method for detection of β-lactamases by using a chromogenic cephalosporin substrate; Antimicrobial Agents and Chemotherapy, Vol. 1, No. 4, 283–288/1972). The inhibition of β-lactamase is tested in 0.1M phosphatebuffer (pH=7.0) using the same substrate. The enzymes are preincubated together with the inhibitors at appropriate concentrations at 25° C. or the inhibitors and the substrate (Nitrocefin) are added simultaneously and the inhibition of substratehydrolysis caused by the inhibitors in comparison to the noninhibited hydrolysis is measured. The activity is expressed in % inhibition or in $IC_{50}$(=concentration of inhibitor, which inhibits 50% of the enzyme).

This inhibiting effect is also noticeable in the marked synergism demonstrated with other β-lactam antibiotics against β-lactamase producing bacteria. The compounds of the present invention are stable to β-lactamases.

The compounds are therefore useful as chemotherapeutics in particular as antibacterially active antibiotics.

For this use the effective dosage will, of course, vary depending on the particular compound employed, mode of administration and the treatment desired. However, in general, satisfactory results can be obtained when the compounds are administered at a daily dosage of from about 15 to 100 mg/kg of animal body weight, suitably given in divided doses two to four times daily. For most larger mammals, the total daily dose is from about 1 to 6 g and dosage froms suitable for internal administration suitably contain 250 to 3000 mg of a compound in admixture with a solid or liquid pharmaceutical carrier or diluent. The compounds of formula I may be administered in similar manner as known standards for use in such indications e.g. Cefotaxim. The suitable daily dosage for a particular compound will depend on a number of factors such as its relative potency of activity. It has for example been determined that a preferred compound of this invention namely (4R,5R,6R)-1-aza-6-[1(R)-fluorethyl]-4-methyl-7-oxo-3-[N,N,N'-trimethylcarbamido)methyl]thiobicyclo[3.2.0-]hept-2-ene-2-carboxylic acid exhibited a curative dose of ca. 1 mg/kg in the model of *Streptococcus septicaemic* infestions in mice compared with 5 mg/kg for Cefotaxim. It is therefore indicated that those compounds may be administered at similar or lower dosages than conventionally employed Cefotaxim.

Compounds which contain a free salt forming group can be employed in this form or in the form of a chemotherapeutically acceptable salt thereof, which forms have the same order of activity as the free forms. Suitable salt forms include alkali and alkaline earth metal and ammonium or amino acid salt forms.

Compounds may be admixed with conventional chemotherapeutically acceptable diluents and carriers, and administered in such forms as tablets or capsules or parenterally. Such compositions also form part of the invention.

The invention therefore also concerns a method of combating bacteria comprising administering to a subject in need of such treatment an effective amount of a compound of formula I or a chemotherapeutically acceptable salt thereof and such compounds for use as chemotherapeutic agents, in particular anti-bacterially active antibiotics.

Lower alkyl moieties contain 1 to 6 (e.g. 1–4) esp. 1 or 2 carbon atoms. Correspondingly alkeny and alkynyl moieties contain 2 to 4 particularly 2 or 3 carbon atoms. Cycloalkyl groups contain preferably 3 to 6 carbon atoms.

By lower acylaminoalkyl is to be understood e.g. —CH$_2$CH$_2$.NH.CO.—C$_2$H$_5$, —CH$_3$; —CH$_2$CH$_2$.NH.CO.CH$_2$.C$_6$H$_5$; —CH$_2$CH$_2$.NH.CO.CH$_2$CH$_2$.NH$_2$; —CH$_2$CH$_2$.NH.CO.CH$_2$.NH$_2$. Heterocycles as R$_7$ include e.g.

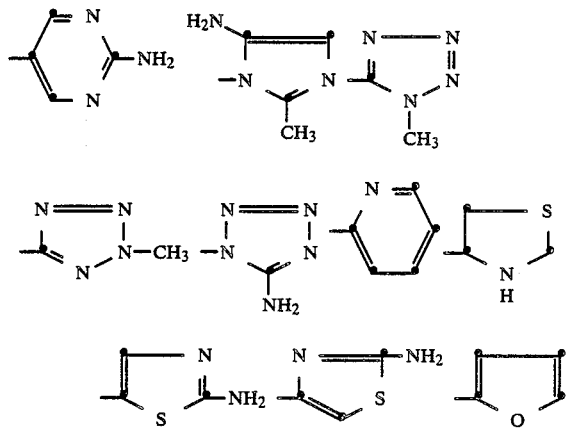

and morpholino.

Protecting groups are those conventionally employed in antibiotics chemistry to protect OH, NH$_2$ and COOH groups. They include p-nitrobenzyl, p-nitrobenzyloxycarbonyl, t-butyl-dimethylsilyl, trimethylsilyl.

Physiologically hydrolysable- and acceptable-ester groups (also known as easily cleavable ester groups) are those which are hydrolysable under physiological conditions to yield acids which are themselves physiologically acceptable, such esters include acetoxymethyl, 1-acetoxyethyl, 1-ethoxycarbonyloxyethyl, 5-indanyl or preferably, pivaloyloxymethyl, hexanoyloxymethyl, phthalidyl, ethoxycarbonylmethoxymethyl or 3-ethoxycarbonyl-1-acetonyl.

It will be appreciated that certain protecting groups can also be physiologically hydrolysable- and acceptable-groups and vice versa.

Preferred substituents are

R$_1$=
  (a) H; (b) CH$_3$

R$_2$=
  (a) lower alkyl optionally mono- or di-substituted by amino, mono- or di-lower alkylamino, acylamino, carboxy
  (b) —(CH$_2$)$_p$—R$_5$
  (c) II, IIa or IIb preferably IIa

R$_3$=H

R$_4$=CH$_3$

R$_5$=
  (a) individual heterocycles as listed above
  (b) methyltetrazolyl, morpholinyl R$_6$,R$_7$,R$_8$=
  (a) H, alkyl especially methyl
  (b) closed rings p=0, 1, 2, 3 preferably 0 or 2 m=2 or 3 preferably 2 n=1, 2, or 3 preferably 1.

Combinations of these meanings and the preferred forms thereof are especially interesting. Examples are $R_1$=hydrogen or methyl; $R_2$=lower alkyl optionally mono- or di-substituted by carboxy, amino, mono- and or di-lower alkyl amino or acylamino; or —$(CH_2)_pR_5$ wherein $R_5$ is a heterocycle, e.g. methyltetrazolyl.

A further example is $R_1$=hydrogen; $R_2$=amino(lower)alkyl, $(CH_2)_pR_5$ wherein $R_5$ represents methyltetrazolyl and p is 2 or IIa wherein $R_6,R_7$ and $R_8$=$CH_3$ and m is 1, $R_3$=H, $R_4$=$CH_3$.

A particularly preferred single compound is (4R,5R,6R)-1-aza-6-[1(R)-fluoroethyl]-4-methyl-7-oxo-3[N,N,N'-trimethylcarbamidino)methyl]thiobicyclo[3.2.0]hept-2-ene-2-carboxylic acid in free form or in the form of a physiologically-hydrolysable and acceptable ester, of a salt or of a zwitter-ion.

The following examples illustrate the invention whereby temperatures are expressed in degrees centigrade.

EXAMPLE 1

(5RS,6RS)-3-(2-aminoethylthio)-1-aza-6-[1(RS)-fluorethyl]-4-methyl-7-oxobicyclo[3.2.0]hept-2-ene-2-carboxylic acid (a) To an ice-cold solution of 130 mg of (5RS,6RS)-1-aza-3,7-dioxo-6-[1(RS)-fluorethyl]-4-methyl-bicyclo[3.2.0]heptane-2-carboxylic acid.4-nitrobenzylester in 20 ml of dichloromethane are added 0.13 ml of ethyl diisopropylamine followed by 146 μl of phosphoric acid diphenyl ester chloride. After 15 minutes at 0° a further 0.13 ml of ethyl diisopropylamine are added followed by 90 mg of 4-nitrobenzyloxycarbonylcysteamine in 5 ml of dichloromethane. Stirring is continued for 1 hour at 0° and the reaction mixture then partitioned between ethyl acetate and saturated aqueous NaCl. After drying over $MgSO_4$ the organic phase is evaporated to dryness and the residue chromatographed over silica gel (eluant: dichloromethane/ether=10/1). (5RS,6RS)-1-aza-6-[1(RS)-fluorethyl]-4-methyl-3-[2-(4-nitrobenzyloxycarbonyl)aminoethylthio]-7-oxobicyclo[3.2.0]hept-2-ene-2-carboxylic acid.4-nitrobenzylester is obtained.

NMR ($CDCl_3$): 1.18–1.40 (m, 4.5); 1.50–1.66 (m, 1.5); 2.69–3.60 (m, 6); 4.06 (dd, 1, J=9, 2.5 Hz); 4.48–4.80 (m, 0.5); 5.00–5.40 (m, 4.5); 7.53 (d, 2, J=9 Hz); 7.56 (d, 2, J=9 Hz); 8.25 (d, 2, J=9 Hz); 8.28 (d, 2, J=9 Hz).

(b) A suspension of 0.1 g of (5RS,6RS)-1-aza-6-[1(RS)-fluorethyl[-4-methyl-3-[2-(4-nitrobenzyloxycarbonyl)aminoethylthio]-7-oxobicyclo[3.2.0]hept-2-ene-2-carboxylic acid.4-nitrobenzylester and 0.1 g of 10% Pd/C in 5 ml of tetrahydrofuran and 5 ml phosphate buffer (pH 7) are hydrogenated at 20° at 1 bar hydrogen pressure for 1 hour. After filtration of the catalyst and washing of the residue with buffer the combined filtrates are extracted with ethylacetate and the aqueous phase freeze-dried. The lyophilisate is purified by chromatography over HP-20. Fractions with UV-extinction at 300 nm are combined and lyophilised to obtain the title compound. UV (pH 7 buffer): λmax.=295 nm.

The following compounds of formula I may be obtained analogously or as hereinbefore described.

| Ex. | $R_1$ | $R_2$ | $R_3$ | $R_4$ | Conf. | phys. chem. data |
|---|---|---|---|---|---|---|
| 2 | H | —$CH_2CH_2$—N(N=N—N=N—CH_3 ring) | H | $CH_3$ | 4R, 5R, 6R, 8R | amorph λmax = 297 |
| 3 | H | —$CH_2CH_2$—N(N=N—N=N—CH_3 ring) | H | $CH_3$ | 4S, 5R, 6R, 8R | amorph λmax = 297 |
| 4 | H | —$CH_2$.C(=NCH_3)(N(CH_3)_2) | H | $CH_3$ | 4R, 5R, 6R, 8R | amorph λmax = 295 |

The 4-nitrobenzylester of the compounds of formula I may be obtained analogously or as hereinbefore described:

| Ex. | COO— | $R_1$ | $R_2$ | $R_3$ | $R_4$ | Conf. |
|---|---|---|---|---|---|---|
| 5 | —$CH_2$—C_6H_4—$NO_2$ | H | —$CH_2CH_2$—N (triazolyl with $CH_3$) | H | $CH_3$ | 4R, 5R, 6R, 8R |
| 6 | —$CH_2$—C_6H_4—$NO_2$ | H | —$CH_2$.C(=$\overset{\oplus}{N}HCH_3$)(N(CH_3)_2)  $C_4F_9SO_3^\ominus$ | H | $CH_3$ | 4R, 5R, 6R, 8R |

NMR Spectra

| Ex. | Spectrum: | |
|---|---|---|
| 2 | ($D_2O$) | 1.11 (d,3,J=7Hz); 1.43 (dd,3,J=25 + 6,5Hz); 2.57 (s,3); 3.09 (dq,1,J=9 + 7Hz); 3.22 (dt,1,J=15 + 5Hz); 3.40 |

| | | -continued |
|---|---|---|
| | | (ddd,1,J=15, 8.5 + 4.5Hz); 3.60 (ddd,1,J=26.5, 5 + 2.5Hz); 3.95 (dd,1,J=9 + 2,5Hz); 4.63 (ddd,1,J=14.5, 8.5 + 4.5Hz); 4.76 (dt,1,J=14.5 + 5Hz); 5.13 (ddq,1,J=47,7 + 5Hz). |
| 4 | (D₂O) | 1.24 (d,3,J=7Hz); 1.44 (dd,3,J=25 + 7Hz); 3.10 (s,3); 3.12 (s,3); 3.34 (s,3); 3.44 (dq,1,J=9.5 + 7Hz); 3.76 (ddd,1,J=28, 5 + 3Hz); 4.00 (d,1,J=14Hz); 4.06 (d,1,J=14Hz); 4.38 (dd,1,J=9.5 + 3Hz); 5.16 (ddq,1,J=48, 7 + 5Hz). |
| 5 | (CDCl₃) | 1.18 (d,3,J=7Hz); 1.48 (dd,3,J=24,5, 6,3Hz); 2.51 (s,3); 3.20–3.55 (m,4); 4.12 (dd,1,J=9, 2,5Hz); 4.40 (ddd,1,J=15, 10, 6,3Hz); 4.65 (dt,1,J=15, 6,3Hz); 5.00 (d of quint.,1,J=49, 6,3Hz); 5.27 (d,1,J=13,7Hz); 5.47 (d,1,J=13,7Hz); 7.65(d,2,J=9Hz); 8.26(d,2,J=9Hz). |
| 6 | (CDCl₃) | 1.14 (d,3,J=6,3Hz); 1.48 (dd,3,J=23,5, 7Hz); 3.00–3.20 (m,7); 3.32 (s,3); 3.46 (ddd,1,J=21,3, 6,3, 2,5Hz); 4.02 (d,1, J=12,5Hz); 4.11 (d,1,J=12,5Hz); 4.35 (dd,1,J=10, 2,5Hz); 5.03 (d of quint.,1,J=47,5, 6,3Hz); 5.26 (d,1,J= 13,8Hz); 5.50(d,1,J=13,8Hz); 7.64(d,2,J=9Hz); 8.23 (d, 2,J=9Hz); 8.90(br, 1). |

The required starting materials can be prepared as follows:

(A) (5RS,6RS)-1-aza-3,7-dioxo-6-[1(RS)-fluorethyl]-4-methylbicyclo[3.2.0]-heptane-2-carboxylic acid.4-nitrobenzylester (for example 1)

(a) (3RS,4RS)-3-[1(RS)-fluorethyl]-2-oxoazetidine-4-yl-acetic acid benzylester

To a −78° cooled solution of 1.5 ml of diethylaminosulphurtrifluoride in 4 ml of dry dichloromethane is added a solution of 2.52 g of (3SR,4RS)-3-[1(SR)-hydroxyethyl]-2-oxoazetidine-4-yl-acetic acid benzyl ester (prepared analogously to D. G. Melillo et.al., Tetrahedron Letters 21, 2783 [1980]) in 4 ml of abs. dichloromethane. The mixture is stirred for 5 minutes at −78° and mixed with excess cold saturated NaHCO₃. After addition of further dichloromethane the phases are separated, the organic phase dried over magnesium sulphate and evaporated to dryness. Chromatography of the residue over silica gel (cyclohexane/ethylacetate=2/1) yields the title compound m.p. 40°–43°.

IR (CHCl₃): 1765, 1730 cm⁻¹

NMR (CDCl₃): 1.45 (dd, 3, J=24, 6.5 Hz); 2.68 (dd, 1, J=16, 9 Hz); 2.86 (dd, 1, J=16, 5.5 Hz); 3.01 (ddd, 1, J=18.5, 7, 2.5 Hz); 4.02 (ddd, 1, J=9, 5.5, 2.5 Hz); 4.97 (dq, 1. J=48, 6.5 Hz); 5.18 (s, 2); 6.25 (br, 1); 7.40 (s, 5).

(b) 2-[(3RS,4RS)-3-[1(RS)-fluorethyl]-2-oxoazetidine-4-yl]propanoic acid benzyl ester To a −78° cooled solution of 1.68 ml diisopropylamine in 12.5 ml of abs. tetrahydrofuran are added 12.5 ml of a 1.6M solution of n-butyl-lithium in hexane. After 20 minutes at −78° 1.32 g of (3RS,4RS)-3-[1(RS)-fluorethyl]-2-oxoazetidine-4-yl-acetic acid benzyl ester are added and after a further 20 minutes 1.87 ml of methyliodide. The reaction mixture is stirred for 40 minutes at −78° and then warmed to 0°. The mixture is diluted with 0.1N HCl and extracted with ethylacetate. The ethylacetate phase is washed once with water and once with saturated NaCl solution, dried over MgSO₄ and concentrated to dryness. Chromatography of the residue over silica gel (dichloromethane/ethylacetate=50.1) yields the title compound.

NMR (CDCl₃): 1.14–1.34 (m, 4.5); 1.48–1.61 (m, 1.5); 2.53–3.32 (m, 2); 3.57–3.84 (m, 1); 4.48–4.62 (m, 0.5); 5.00–5.20 (m, 2.5); 6.33 (br, 1); 7.34 (br, s, 5).

(c) 2-[(3RS,4RS)-3-[1(RS)-fluorethyl]-2-oxoazetidine-4-yl]propionic acid

A mixture of 500 mg of the corresponding benzylester and 50 mg of 10% Pd/C in 50 ml of methanol is hydrogenated at a hydrogen pressure of 1 bar for 1 hour. Filtration and concentration of the filtrate to dryness yields the title compound.

NMR (CDCl₃): 1.17–1.40 (m, 4.5); 1.53–1.67 (m, 1.5); 2.48–3.36 (m, 2); 3.64–4.00 (m, 1); 5.10–5.36 (m, 0.5); 4.00–4.90 (m, 1.5).

(d) 4-[(3RS,4RS)-3-[1(RS)-fluorethyl]-2-oxoazetidine-4-yl]-3-oxopentanoic acid.4-nitrobenzylester 200 mg of 2-[(3RS,4RS)-3-[1(RS)-fluorethyl]-2-oxoazetidine-4-yl]propanoic acid are dissolved in 8 ml of tetrahydrofuran, treated at −78° with 280 mg of carbonyldiimidazole and stirred for 3 hours at 20°. At the same time 550 mg of malonic acid 4-nitrobenzylester and 200 ml of magnesium ethoxide are suspended in 8 ml of tetrahydrofurane and stirred for 3 hours at RT. The first solution is then added to the second and the mixture stirred overnight. The result is poured into ether and extracted with 1N HCl and water. Drying of the organic phase followed by column chromatography of the residue yields the title compound.

NMR (CDCl₃): 1.10–1.34 (m, 4.5); 1.52–1.63 (m, 1.5); 2.44–3.07 (m, 2); 3.48 (s, 0.5); 3.60 (s, 1.5); 3.67–3.95 (m, 1); 4.46–4.74 (m, 0.5); 5.04–5.34 (m, 2.5); 6.06 (br, 1); 7.52 (d, 2, J=9 Hz); 8.24 (d, 2, J=9 Hz).

(e) 4-[(3RS,4RS)-3-[1(RS)-fluoroethyl]-2-oxoazetidine-4-yl]-2-diazo-3-oxo-pentanoic acid.4-nitrobenzylester To an ice cooled solution of 0.16 g 4-[(3RS,4RS)-3-[1(RS)-fluorethyl]-2-oxoazetidine-4-yl]-3-oxopentanoic acid.4-nitrobenzylester and 0.12 g of 4-carboxybenzenesulfonylazide in 8 ml of acetonitrile are added 0.24 ml of triethylamine. After removal of the cooling bath stirring is carried out for 30 minutes at room temperature. The mixture is poured into 100 ml of ethyl acetate, washed with 5% NaHCO₃ solution and then with water and dried over MgSO₄. Removal of the solvent yields the title compound.

NMR (CDCl₃): 1.08–1.40 (m, 4.5); 1.53–1.66 (m, 1.5); 2.82–3.20 (m, 1); 3.46–4.04 (m, 2); 4.92 (dm, 1, J=48.5 Hz); 5.38 (s, 2); 5.90–6.20 (br, 1); 7.57 (d, 2, J=9 Hz); 8.30 (d, 2, J=9 Hz).

(f) (5RS,6RS)-1-aza-3,7-dioxo-6-[1(RS)-fluorethyl]-4-methylbicyclo-[3.2.0]heptane-2-carboxylic acid.4-nitrobenzylester A suspension of 0.15 g of 4-[(3RS,4RS)-3-[1(RS)-fluorethyl)]-2-oxoazetidine-4-yl]-2-diazo-3-oxopentanoic acid.4-nitrobenzylester and 3 mg of rhodiumacetate in 70 ml of benzene is warmed for 20 minutes at 80° under argon. After cooling to room temperature the catalyst is filtered off and the filtrate concentrated to dryness to obtain the title compound.

NMR (CDCl₃): 1.17–1.42 (m, 4.5); 1.50–1.62 (m, 1.5); 2.20–2.98 (m, 1); 3.20–3.60 (m, 1); 3.78 (dd, 0.75, J=8.5, 2 Hz); 4.28 (dd, 0.25, J=7.5, 2 Hz); 4.66–4.94 (m, 1.5); 5.20–5.50 (m, 2.5); 7.57 (d, 2, J=9 Hz); 8.30 (d, 2, J=9 Hz).

(B) 4(R)-[(3R,4R)-3-[1(R)-fluorethyl]-2-oxoazetidine-4-yl]-3-oxo-pentanoic acid.4-nitrobenzylester and 4(S)-[(3R,4R)-3-[1(RS)-fluorethyl]-2-oxoazetidine-4-yl]-3-oxo-pentanoic acid.4-nitrobenzylester:

(a) 6-trans-1(S)-hydroxyethylpenicillanic acid.benzhydrylester

To a solution of 14 g of diazopenicillanic acid.benzhydrylester in 50 ml of dichlormethane are added 20 mg of zinc chloride, the mixture cooled to −10°, 18 ml of freshly distilled acetaldehyde slowly added dropwise and the result stirred for a further hour. The reaction mixture is then washed once with pH 7 buffer solution once with saturated NaCl solution, dried over MgSO₄, filtered and concentrated. The residual oil is dissolved in 200 ml of dry tetrahydrofuran, cooled to −78°, treated with 36 ml of Superhydride ® and then stirred for a further 30 minutes. The mixture is then diluted with ethylacetate, washed once with pH 7 buffer, once with water, once with saturated NaCl solution, dried over MgSO₄ and after removal of the solvent chromatographed on silica gel (dichloromethane/ether=10.1). The title compound is obtained as a crystalline product m.p. 63°–66°.

NMR (CDCl₃): 1.22 (s, 3); 1.34 (d, 3, J=6.8 Hz); 1.60 (s, 3); 2.00 (br, 1); 3.40 (dd, 1, J=6.3, 2 Hz); 4.06–4.38 (m, 1); 4.57 (s, 1); 5.28 (d, 1, J=2 Hz); 6.95 (s, 1); 7.18–7.48 (m, 10).

(b) 6-trans-1(R)-fluoroethylpenicillanic acid.benzhydrylester

To a suspension of 4.33 g potassium fluoride in 200 ml of dry dichloromethane are added at −78° under argon 10 ml of diethylamino sulphurtrifluoride. To this suspension is now added at −78° a chilled solution (−78°) of 13.5 g of 6-trans-1(S)-hydroxyethylpenicillanic acid.-benzhydrylester. After one hour at −78° the cooling bath is removed and stirring continued for 1 more hour at room temperature. For working-up the mixture is extracted twice with water dried over MgSO₄ and concentrated. The residue is chromatographed on silica gel (dichloromethane/petroleum ether=10/3 to obtain the oily title compound.

NMR (CDCl₃): 1.25 (s, 3); 1.47 (dd, 3, J=23.5, 6.3 Hz); 1.62 (s, 3); 3.47 (ddd, 1, J=20.7, 7.2, 1.8 Hz); 4.59 (s, 1); 5.00 (ddq, 1, J=49.6, 7.2, 6.3 Hz); 5.36 (d, 1, J=1.8 Hz); 6.97 (s, 1); 7.22–7.25 (m, 10).

(c) 2-[4-acetoxy-(3R)-3-[1(R)-fluorethyl]-2-oxoazetidine-1-yl]-3-methyl-2-butenoic acid.benzhydrylester To a solution of 0.98 g of 6-trans-1(R)-fluoroethylpenicillaic acid.benzhydrylester in 30 ml of acetic acid are added 2.28 g of mercury (II) acetate and stirring carried out for 1 hour at 100°. After cooling filtration is performed and the filtrate brought to dryness and stirred three more times with toluene. The residue is taken up in ethylacetate and insolubles again filtered off. The filtrate is extracted three times each with 20 ml water, dried over MgSO₄ and concentrated. The residue is chromatographed on silica gel (dichloromethane/ether=30/1) to obtain the title compound m.p. 102°–105°.

IR (CHCl₃): 1770, 1720 cm⁻¹.

(d) 4-Acetoxy-(3R)-3-[1(R)-fluorethyl]-2-oxoazetidine

Ozone is passed through a solution of 6.2 g of 2-[4-acetoxy-(3R)-3-[1(R)-fluorethyl]-2-oxoazetidine-1-yl]-3-methyl-2-butenoic acid.benzhydrylester at −78° until a permanent blue colour is achieved. The excess ozone is drive out with nitrogen and 1.75 g of dimethylsulphide added. The reaction mixture is allowed to rise to room temperature. The solvent is evaporated on a rotary evaporator, the residue taken up in 100 ml of methanol and after addition of 2 drops of triethylamine stirred for 2 hours. After renewed concentration the residue is chromatographed on silica gel (dichloromethane/ethylacetate=10/3) to obtain the oily title compound.

IR (CHCl₃): 3420, 1785, 1745 cm⁻¹.

(e) 2(R)-[(3R,4R)-3-[1(R)-fluorethyl]-2-oxoazetidine-4-yl]monothiopropanoic acid.S-phenylester and 2(S)-[(3R,4R)-3-[1(R)-fluorethyl]-2-oxazetidine-4-yl]monothiopropanoic acid.S-phenylester To a solution of 1.8 ml of diisopropylamine in 30 ml of dry tetrahydrofuran are added at −78° 7.79 g of butyllithium solution (1.6M) in hexane. After 30 minutes 1.95 g of monothiopropanoic acid.S-phenylester in 10 ml of tetrahydrofuran are added. The faintly yellow solution in stirred for 30 minutes at −78°, 2.25 ml of trimethylchlorosilane then added and the mixture allowed to rise to room temperature. After removal of the solvent the residue is digested in pentane, filtered under argon and again concentrated. To the remaining yellow liquid are added 5 ml of dry acetonitrile and 700 mg of 4-acetoxy-(3R)-3-[1(R)-fluorethyl]-2-oxoazetidine dissolved in 1 ml of dry acetonitrile. The solution is cooled to −30° and 0.16 ml trifluoromethanesulfonic acid trimethylsilyl ester injected in. The reaction mixture is allowed to rise to room temperature and stirred for 20 hours at this temperature. It is then poured onto pH 7 buffer and extracted with ethylacetate, dried over Na₂SO₄ and concentrated. Chromatography over silica gel (ethylacetate/cyclohexane=1/1) yields the title compound as 1:1 mixture which can be separated by chromatography.

NMR for 2(R)-Isomer (CDCl₃); 1.34 (d, 3, J=6.5 Hz); 1.50 (dd, 3, J=24+6.5 Hz); 3.10 (quint., 1, J=6.5 Hz); 3.27 (ddd, 1, J=21, 6.5+2 Hz); 3.92 (dd, 1, J=6.5+2 Hz); 4.97 (d of quint., 1, J=48.5+6.5 Hz); 6.28 (br, 1); 7.44 (s, 5).

NMR for 2(S)-Isomer (CDCl₃); 1.39 (d, 3, J=7 Hz); 1.50 (dd, 3, J=24.5+6.3 Hz); 2.90 (dq, 1, J=9+7 Hz); 3.01 (dddd, 1, J=17, 8.5, 2+0.5 Hz); 3.80 (dd, 1, J=9+2 Hz); 4.93 (ddq, 1, J=48.5, 8.5+6.3 Hz); 6.26 (br, 1) 7.46 (s, 5).

(f) 2(R)-[(3R,4R)-3-[1(R)-fluorethyl]-2-oxoazetidine-4-yl]propanoic acid and 2(S)-[(3R,4R)-3-[(1(R)-fluorethyl]-2-oxoazetidine-4-yl]propanoic acid A mixture of 290 mg of 2(R)-[(3R,4R)-3-[1(R)-fluorethyl-2-oxoazetidine-4-yl]monothiopropanoic acid.S-phenylester and 2(S)-[(3R,4R)-3-[1(R)-fluorethyl]-2-oxoazetidine-4-yl]monothiopropanoic acid.S-phenylester and 430 mg of mercury (II) trifluoroacetate in 5 ml of dichloromethane is stirred for 4 hours at room temperature. The result is concentrated to dryness and the residue taken up in 10 ml of ice/water. After adjustment of pH of 8.5 (1N NaOH) stirring at room temperature is carried out until the pH value no longer changes. The mixture is then extracted once with ethylacetate and the aqueous phase adjusted to pH 2 and again extracted with ethylacetate. After drying and concentration of this phase the mixture of the title compounds remains, which can be directly further employed.

(g) 4(R)-[(3R,4R)-3-[1(R)-fluorethyl]-2-oxoazetidine-4-yl]-3-oxopentanoic acid.4-nitrobenzylester and 4(S)-[(3R,4R)-3-[1(R)-fluorethyl]-2-oxoazetidine-4-yl]-3-oxopentanoic acid.4-nitrobenzylester Proceed analogously to A(d). The resulting mixture of the two isomeric title compounds is separated by chromatography on silica gel (dichloromethane/ether=10/6) and fractional crystallisation.

| NMR for 4(S)—Isomer(CDCl₃)(keto/enolform = 2/1): | |
| --- | --- |
| 1.23 (d, J = 7.5, keto) | } 3 H |
| 1.26 (d, J = 7.5 Hz, enol) | |
| 1.30 (dd, J = 25 u. 6,5 Hz, enol) | } 3 H |
| 1.33 (dd, J = 25 u. 6,5 Hz, keto) | |
| 2.50 (quint., J = 7,5 Hz, enol) | } 2 H |
| 2.95-3.24 (m, keto/enol) | |
| 3.64 (d, J = 17,5 Hz, keto) | } 1,4 H |
| 3.68 (d, J = 17,5 Hz | |
| 3.83 (dd, J = 7,5 u. 2 Hz, enol) | } 2 H |
| 3.97 (dd, J = 6 u. 2 Hz, keto) | |
| 4.94 (dm, 1, J = 47,5 Hz) | |
| 5.18 (s, 0,3 H, enol) | |
| 5.29 (s, 2) | |
| 6.41 (br, 1) | |
| 7.54 (d, 2, J = 8 Hz) | |
| 8.25 (d, 2, J = 8 Hz) | |
| 11.95 (s, 0,3 H, enol) | |
| NMR for 4(R)—Isomer(CDCl₃)(keto/enolform = 2/1): | |
| 1.26 (d, 3, J = 7,5 Hz) | |
| 1.50 (dd, 3, J = 25 u. 7 Hz) | |
| 2.41 (dq, J = 10 u. 7,5 Hz, enol) | } 1 H |
| 2.76 (dq, J = 10 u. 7,5 Hz, keto) | |
| 2.93 (ddd, J = 15, 8 u. 2 Hz, keto) | } 1 H |
| 3.00 (ddd, J = 16,3, 8 u. 1.8 Hz, enol) | |
| 3.69 (s, keto)1,4 H | |
| 3.72 (dd, J = 10 u. 1,8 H, enol) | } 1 H |
| 3.75 (dd, J = 10 u. 2 Hz, keto) | |
| 4.90 (dm, 1, J = 47,5 Hz) | |
| 5.18 (s, 0,3 H, enol) | |
| 5.29 (s,2) | |
| 6.0 (s, 0,3 H, enol) | |
| 6.08 (br, enol) | } 1 H |
| 6.16 (br, keto) | |
| 7.55 (d, 2, J = 9 Hz) | |
| 8.25 (d, 2˙J = 9 Hz) | |

(C) (4R,5R,6R)-1-aza-3,7-dioxo-6-[1(R)-fluorethyl]-4-methylbicyclo[3.2.0]heptane-2-carboxylic acid.4-nitrobenzylester (a) 4(R)-[(3R,4R)-3-[1(R)-fluorethyl]-2-oxoazetidine-4-yl]-2-diazo-3-oxopentanoic acid.4-nitrobenzylester Proceed analogously to A(e), using 4(R)-[(3R,4R)-3-[(R)-fluorethyl]-2-oxoazetidine-4-yl]-3-oxopentanoic acid.4-nitrobenzylester as starting material, to obtain the title compound.

NMR (CDCl₃): 1.20 (d, 3, J=7 Hz); 1.46 (dd, 3, J=24+6.5 Hz); 3.17 (ddd, 1, J=20, 6.8°2 Hz); 3.86–4.00 (m, 2); 4.93 (d of quint. 1, J=48+6.5 Hz); 5.35 (d, 1, J=15 Hz); 5.39 (d, 1, J=15 Hz); 6.00 (br, 1); 7.56 (d, 2, J=8 Hz); 8.29 (d, 2, J=8 Hz).

(b) (4R,5R,6R)-1-aza-3,7-dioxo-6[1(R)-fluorethyl]-4-methylbicyclo[3.2.0]heptane-2-carboxylic acid.4-nitrobenzylester Proceed analogously to A(f), using the compound obtained under C(a) as starting material, to obtain the title compound.

NMR (CDCl₃): 1.30 (d, 3, J=8 Hz); 1.53 (dd, 3, J=23.3+6.3 Hz); 2.86 (quint., 1, J=8 Hz); 3.42 (ddd, 1, J=17.5, 7.5+2 Hz); 4.28 (dd, 1, J=8+2 Hz); 4.76 (s, 1); 5.09 (ddq, 1, J=47.5, 7.5+6.3 Hz); 5.27 (d, 1, J=12.5 Hz); 5.37 (d, 1, J=12.5 Hz); 7.55 (d, 2, J=8 Hz); 8.46 (d, 2, J=8 Hz).

(D) (4S,5R,6R)-1-aza-3,7-dioxo-6[1(R)-fluorethyl]-4-methylbicyclo[3.2.0]heptane-2-carboxylic acid.4-nitrobenzylester (a) 4(S)-[(3R,4R)-3-1(R)-fluorethyl]-2-oxoazetidine-4-yl]-2-diazo-3-oxopentanoic acid.4-nitrobenzylester Proceed analogously to A(e), using 4(S)-[(3R,4R)-3-[1(R)-fluorethyl]-3-oxopentanoic acid.4-nitrobenzylester as starting material, to obtain the title compound.

NMR (CDCl₃): 1.22 (d, 3, J=7.2 Hz); 1.49 (dd, 3.J=24.5+6.3 Hz); 3.01 (ddd, 1, J=16, 7.5+2 Hz); 3.56 (dq, 1, J=9+7.2 Hz); 3.92 (dd, 1, J=9+2 Hz); 4.91 (ddq, 1, J=48.5, 7.5+6.3 Hz); 5.36 (d, 1, J=13.8 Hz); 5.39 (d, 1, J=13.8 Hz); 5.98 (br, 1); 7.56 (d, 2, J=9 Hz); 8.29 (d, 2, J=9 Hz).

(b) (4S,5R,6R)-1-aza-3,7-dioxo-6-[1(R)-fluorethyl]-4-methylbicyclo[3.2.0]heptane-2-carboxylic acid.4-nitrobenzylester Proceed analogously to A(f), using the producing obtained under D(a) as starting material, to obtain the title compound.

NMR (CDCl₃): 1.30 (d, 3, J=7 Hz); 1.54 (dd, 3, J=25+6.3 Hz); 2.40 (dq, 1, J=8+7 Hz); 3.39 (ddd, 1, J=18, 7.5+1.8 Hz); 3.76 (dd, 1, J=8+1.8 Hz); 4.84 (s, 1); 5.10 (ddq, 1, J=49, 7.5+6.3 Hz); 5.27 (d, 1, J=12.5 Hz); 5.36 (d, 1, J=12.5 Hz); 7.55 (d, 2, J=9 Hz); 8.25 (d, 2, J=9 Hz).

We claim:

1. A compound of the formula

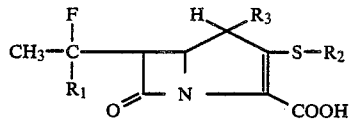

wherein
R₁ is hydrogen or methyl,
R₂ is a substituent of the formula

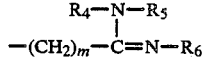

or —(CH₂)$_n$—R₇,
R₃ is methyl,
R₄, R₅ and R₆ are hydrogen or methyl, and
R₇ is —NH₂,
m is 1, 2 or 3, and
n is 0, 1, 2 or 3,
or a salt thereof or a zwitterion thereof.
2.

17

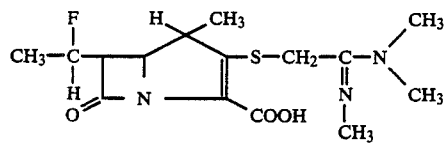

or a protected form thereof, and/or a physiologically hydrolyzable and acceptable ester thereof or a zwitterion thereof.

3.

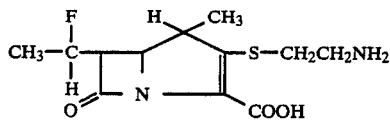

or a protected form thereof, and/or a physiologically hydrolyzable and acceptable ester thereof or a zwitterion thereof.

18

4.

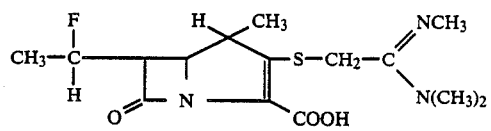

or a protected form thereof, and/or physiologically hydrolyzable and acceptable ester thereof or a zwitterion thereof.

5. An antimicrobial composition comprising an effective amount of a compound according to claim 1 or a pharmaceutically acceptable salt or zwitterion thereof together with a pharmaceutically acceptable diluent or carrier.

6. A method of combating bacteria which comprises administering to a subject in need of such treatment an effective amount of a compound according to claim 1 or a pharmaceutically acceptable salt or zwitterion thereof together with a pharmaceutically acceptable diluent carrier.

* * * * *

UNITED STATES PATENT AND TRADEMARK OFFICE
CERTIFICATE OF CORRECTION

PATENT NO. : 4,720,491

DATED : January 19, 1988

INVENTOR(S) : Ching P. MAK et al.

It is certified that error appears in the above-identified patent and that said Letters Patent is hereby corrected as shown below:

In the Assignee Data, that portion reading "Sandoz Ltd." should read --Sanraku Incorporated---.

Signed and Sealed this

Twelfth Day of July, 1988

Attest:

DONALD J. QUIGG

Attesting Officer     Commissioner of Patents and Trademarks